(12) United States Patent
Sevack et al.

(10) Patent No.: US 8,545,753 B2
(45) Date of Patent: *Oct. 1, 2013

(54) ULTRA-VIOLET LAMP AND REFLECTOR/SHIELD ASSEMBLY

(75) Inventors: David Sevack, Hampstead (CA); Normand Brais, Rosemère (CA); Stuart Engel, Cote St. Luc (CA)

(73) Assignee: Sanuvox Technologies, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/180,096

(22) Filed: Jul. 11, 2011

(65) Prior Publication Data

US 2012/0023992 A1   Feb. 2, 2012

Related U.S. Application Data

(60) Continuation of application No. 12/750,197, filed on Mar. 30, 2010, now Pat. No. 7,976,195, which is a continuation of application No. 12/195,048, filed on Aug. 20, 2008, now Pat. No. 7,837,933, which is a continuation of application No. 11/109,075, filed on Apr. 18, 2005, now abandoned, which is a division of application No. 09/876,413, filed on Jun. 7, 2001, now abandoned.

(30)   Foreign Application Priority Data

Jul. 6, 2000   (CA) .................................... 2310792

(51) Int. Cl.
*A61L 2/10* (2006.01)
(52) U.S. Cl.
USPC ............................. 422/24; 96/55; 250/432 R
(58) Field of Classification Search
USPC .............. 362/275, 287; 422/121, 24; 96/55; 250/432 R
See application file for complete search history.

(56)   References Cited

U.S. PATENT DOCUMENTS

| 5,330,722 A | * | 7/1994 | Pick et al. .......................... 96/55 |
| 5,780,860 A | * | 7/1998 | Gadgil et al. .............. 250/432 R |
| 6,500,387 B1 | * | 12/2002 | Bigelow .......................... 422/24 |

* cited by examiner

*Primary Examiner* — Lam S Nguyen
(74) *Attorney, Agent, or Firm* — Michael Best & Friedrich LLP; Paul A. Jenny; Todd S. Hofmeister

(57)   ABSTRACT

An ultra-violet lamp and reflector/shield assembly designed to be mounted in a commercial HVAC, and to other types of A/C units is described herein. The reflector/shield includes a reflective inner surface creating an illumination pattern and an outer surface shielding the UV lamp from the air flow. An orienting and securing assembly for a UV lamp is also described herein.

6 Claims, 10 Drawing Sheets

ULTRA-VIOLET LAMP AND REFLECTOR/SHIELD ASSEMBLY

FIELD OF THE INVENTION

The present invention relates to ultra-violet (UV) lamps. More specifically, the present invention is concerned with an assembly including a UV lamp and a reflector/shield allowing the lamp to be used in commercial type HVAC coils and in other types of coil systems.

BACKGROUND OF THE INVENTION

Indoor Air Quality related problems, often referred to as "SICK BUILDING SYNDROMES" costs North America well over 100 Billion dollars each year in health care, absenteeism, lost production time and lost revenue.

Buildup of biological contaminants such as bacteria and molds onto the air conditioning coils has been identified as a major cause of the sick building syndrome. Those living organisms eventually release their toxins in the indoor air. Even in very small quantities, these toxins are extremely potent and can trigger violent responses from the human immune system. Such symptoms are commonly called allergies. The microorganisms found in buildings or workplace are viruses, bacteria, and their components, such as endotoxins, fungi and their metabolic products such as mycotoxins and antigens.

Most environments contain a large variety of bacteria. Health risks increase only when the pathogens bacteria concentration is amplified in an indoor environment and these organisms or their by-products are suspended and successfully airborne towards the breathing zone. Legionnaire's disease, some pneumonias, and tuberculosis are airborne infectious diseases caused by bacteria (see table 1). Bacteria can also cause humidifier fever and hypersensitivity pneumonitis.

Endotoxins are components of a bacterial cell. More precisely, they are components of the outer membrane of some bacteria. Dangerous levels of airborne endotoxins have been reported in numerous work environments, including offices and laboratories. They can cause fever and malaise, changes in white blood cell counts, and respiratory and gastrointestinal problems (see table 1).

Fungi exist in over 100 000 known species. Microscopic fungi include yeasts and molds. Most fungi produce spores (structures whose role is propagation) that are carried by the air. The diameter of these spores varies from approximately 1 to 60 microns. Most substances containing carbon, abundant in indoor and outdoor environments, can serve as nutrients for molds. Accumulation of humidity in the indoor environment is the most important factor to be controlled to limit fungal growth.

Some fungi can invade living cells and cause infectious diseases. However, several molds produce proteins or glycoproteins that are highly antigenic i.e. capable of producing an immune response and can cause, as reactions, hypersensitivity diseases or allergies in susceptible individuals. These allergy reactions include rhinitis, allergic asthma and extrinsic allergic alveolitis. Growing molds may also produce several volatile organic compounds. These volatile compounds cause the characteristic moldy odour, among other things.

Antigens are organic substances capable of producing an immune response in humans. Practically all living organisms contain proteins; glycoproteins or polysaccharides with antigenic potential. This is a reason why several microorganisms (bacteria, fungi, protozoa, acarids, etc.) have an impact on health via the action of antigens on the immune system.

Of all the hyper sensibility diseases, only hypersensitivity pneumonitis, allergic asthma, allergic rhinitis and allergic aspergillosis are known as being a result of exposure to airborne antigens. The cause effect relationship for microbial allergens is well known, but the complete characterization of the dose-response relationship is not.

Water reservoirs and air conditioning units cooling coils where warm water condenses are good growth media for some bacteria, fungi or protozoa. Consequently, ventilation system components, particularly some types of humidifiers, can aerosolize droplets from water reservoirs and therefore are of special interest due to the production of small antigenic hypersensitivity pneumonitis have occurred in individuals when building humidification systems were contaminated.

In buildings, the most important sources of antigens relating to human health are mites, cockroaches, and molds. All these organisms produce antigens, which can cause allergic asthma and allergic rhinitis. Dust mites (acarids) and their droppings that have accumulated in bedding, furniture or in places where the relative humidity and temperature are favourable, also produce antigens.

TABLE 1

Biological air contaminants

| Biological contaminants | Health Effects | Major Indoor Sources |
|---|---|---|
| Bacteria | Pneumonia, Fever, Hypersensitivity, Asthma, Pneumonitis | Water reservoirs, hot water or hot surfaces, humidifier, cooling coils |
| Fungi | Asthma, Rhinitis, infections, cancer | Outdoor air, spores, birds, plants, damp surfaces, cooling coils |
| Protozoa | Infection | Water reservoir, humidifier |
| Viruses | Infection | Water reservoir, humidifier |
| Algae | Asthma, Rhinitis | Outdoor Air |
| Green Plants | Asthma, Rhinitis | Outdoor air, pollen |
| Arthropods | Asthma, Rhinitis | Carpets, feces, mattresses, dust |
| Mammals | Asthma, Rhinitis | Dogs, cats, skin scales, saliva |

The Indoor Air Quality Problem

It is now common knowledge that the energy efficient designs of the 1970's resulted in tighter building envelopes with improved insulation and low energy consuming ventilation, without operable windows, and that under these conditions, indoor pollutants were not sufficiently diluted with fresh air. Furthermore, an increase in indoor pollutant sources have been noted. New building materials, products, and furnishing emit a significant number of potentially hazardous chemicals into the air. The resulting situation is an increase in contaminants circulating through the indoor environment, with insufficient outside air introduced to dilute the contaminants.

Indoor air quality (IAQ), is a complex issue, much more so than any single environmental issue. There are hundreds of pollutants that affect IAQ and thousands of sources. Research indicates that more than 900 different contaminants are present in indoor environments.

If needs for comfort, health, and well-being are not satisfied, building users may begin to complain of symptoms which are associated with poor IAQ. Headaches, burning and itching eyes, respiratory difficulties, skin irritation, nausea, congestion, cough, sneezing, and fatigue are some of the common complaints. One of the most common IAQ complaints is that "there's a funny smell in here". Odors are often associated with a perception of poor air quality.

An increasing percentage of the population is becoming more sensitive to a number of chemicals in indoor air, each of which may occur at very low concentrations. The existence of this condition has been identified as Multiple Chemical Sensitivity (MCS) and is currently the object of medical research.

According to EPA, the effects of Indoor IAQ problems are often non-specific symptoms rather than clearly defined illnesses. Although they can be vague, the symptoms seem generally worse after a day in the workplace and may altogether disappear when the occupant leaves the building.

Legionnaire's disease, tuberculosis and hypersensitivity pneumonitis are examples of building related illness that can have serious, even life-threatening consequences.

In light of this, it is easily understandable why indoor air needs to be efficiently purified from biological contaminants.

U.S. Pat. No. 5,817,276 entitled "*Method of UV distribution in an air handling system*" issued on Oct. 6, 1998 and naming Forrest B. Fencl at al., as inventors, describes a system where UV lamps are positioned in a HVAC system downstream of the heat exchanger coil, thus facing the air flow.

Fencl's method has at least four major drawbacks.

Direct air flow on the UV lamp cools it down by convection. A cooler lamp will display a lower UV output. Measurements by lamp manufacturers have shown that the germicidal UV emission drops by as much as 50% when direct air velocity over the lamp goes from 100 ft/min to 700 ft/min. To obtain the same UV irradiation, one must use twice the number of lamps or use expensive and short-life hot lamps with plasma arc temperature booster. Facing the flow, the lamps can collect some oily aerosols and dirt that will further inhibit their UV emission overtime.

By placing the UV lamps facing the outlet of the cooling coil, the inlet face where most of the water condensation and where most of the dust and other bacteria nutrients are normally accumulated is not directly irradiated. Its irradiation relies on the UV reflectivity of the coil material. It is at best 60% when the coil is made of clean aluminum. As the coil gets dirty, this UV reflection coefficient drops very quickly. Fencl is relying on the coil material UV reflection properties to achieve good results. This is a parameter that Fencl cannot control and that can dramatically impair the effectiveness of the invention.

Fencl states that the lamps must be placed over the coil surface in such a way as to provide a uniform irradiation distribution across the coil. Since the condensed water runs down the coil by gravity, the molds and bacteria concentration is most likely to occur at the bottom of the coil. In that view, a uniform irradiation pattern is certainly not the most efficient for the circumstances.

The use of a flat surface (see Fencl's FIG. 4) as a back reflector for the UV lamp allows for the loss of a large portion of the UV radiation. Even if the lamp is mounted very close to the coil, which is not very well suited for a "uniform irradiation", a portion of the radiation that lies behind the 180 degree sector facing the coil cannot be reflected and will be lost.

By placing lamps on the plane perpendicular to the coil to provide uniform irradiation, the bottom area and coil corners where the water runs will not be sufficiently irradiated by the ultraviolet lamps and bacteria and mold will grow in these areas.

Furthermore, by irradiating the coil with an "open" lamp, the UV rays are allowed to irradiate and ultimately destroy any plastic or rubber parts in the air handler that the UV rays contact. Examples of such parts include wires, controls, flexible ducts and plastic drain pans.

OBJECTS OF THE INVENTION

An object of the present invention is therefore to provide an improved UV lamp and shield assembly.

SUMMARY OF THE INVENTION

According to an aspect of the present invention, there is provided an orienting and securing assembly for an ultra-violet lamp assembly; said orienting and securing assembly comprising:
a mounting plate provided with an ultra-violet lamp receiving aperture;
a supporting plate so mounted to said mounting plate as to pivot between a non securing position and a securing position; wherein, when said supporting plate is in said securing position, it is configured to secure a portion of the ultra-violet lamp assembly between the mounting plate and the supporting plate.

According to another aspect of the present invention, there is provided an orienting and securing assembly for an ultra-violet lamp assembly; said orienting and securing assembly comprising:
a round support configured and sized to receive the ultra-violet lamp assembly;
a mounting plate provided with an ultra-violet lamp receiving aperture and two bolts; and
a supporting plate so mounted to said two bolts of said mounting plate as to pivot between a non securing position and a securing position; said orienting and securing assembly further comprising two washers provided on said bolts between the supporting and mounting plates to allow said round support to rotate thereon;
wherein, when said supporting plate is in said securing position, it is configured to secure a portion of said round support between the mounting plate and the supporting plate.

According to another aspect of the present invention, there is provided an orienting and securing assembly to orient and mount an ultra-violet lamp assembly, to a HVAC system, the ultra-violet lamp assembly including a reflector/shield directing ultra-violet radiation; said orienting and securing assembly comprising:
a round support configured and sized to receive the ultra-violet lamp assembly and the reflector/shield;
a mounting plate provided with an ultra-violet lamp receiving aperture and two bolts, said mounting plate being so configured and sized as to be mounted to a wall of the HVAC system; and
a supporting plate so mounted to said two bolts of said mounting plate as to pivot between a non securing position and a securing position; said orienting and securing assembly further comprising two washers provided on said bolts between the supporting and mounting plates to allow said round support to rotate thereon;
wherein, a) when said supporting plate is in said non securing position, said round support may be rotated to prevent ultra-violet radiation to reach elements of the HVAC that are made of material sensitive to ultra-violet radiation; and b) when said supporting plate is in said securing position, a portion of said round support is secured between the mounting plate and the supporting plate.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings.

FIG. 3 is a perspective view Illustrating a system of UV lamp assemblies including four UV lamp assemblies as shown in FIG. 1 mounted to a support and facing the coil of a HVAC system;

DETAILED DESCRIPTION

Figure 1:
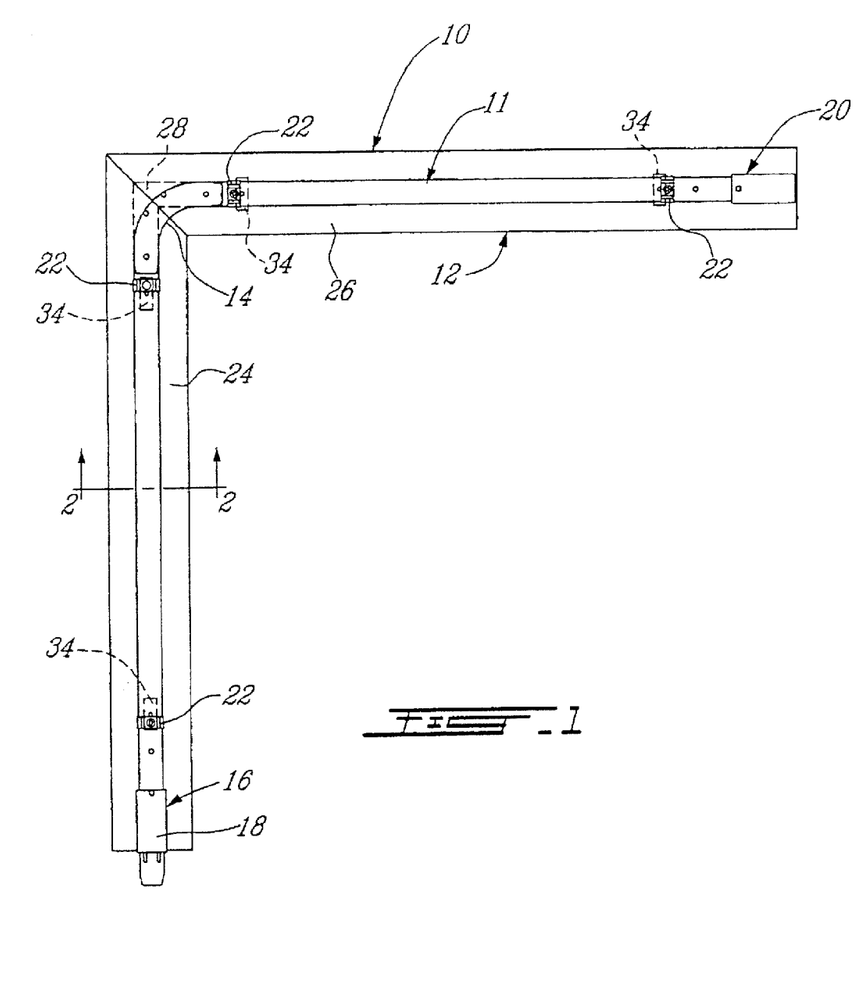
FIG. 1 is a front elevational view of an assembly comprising a L-shaped UV lamp provided with a reflector/shield.
Figure 2:
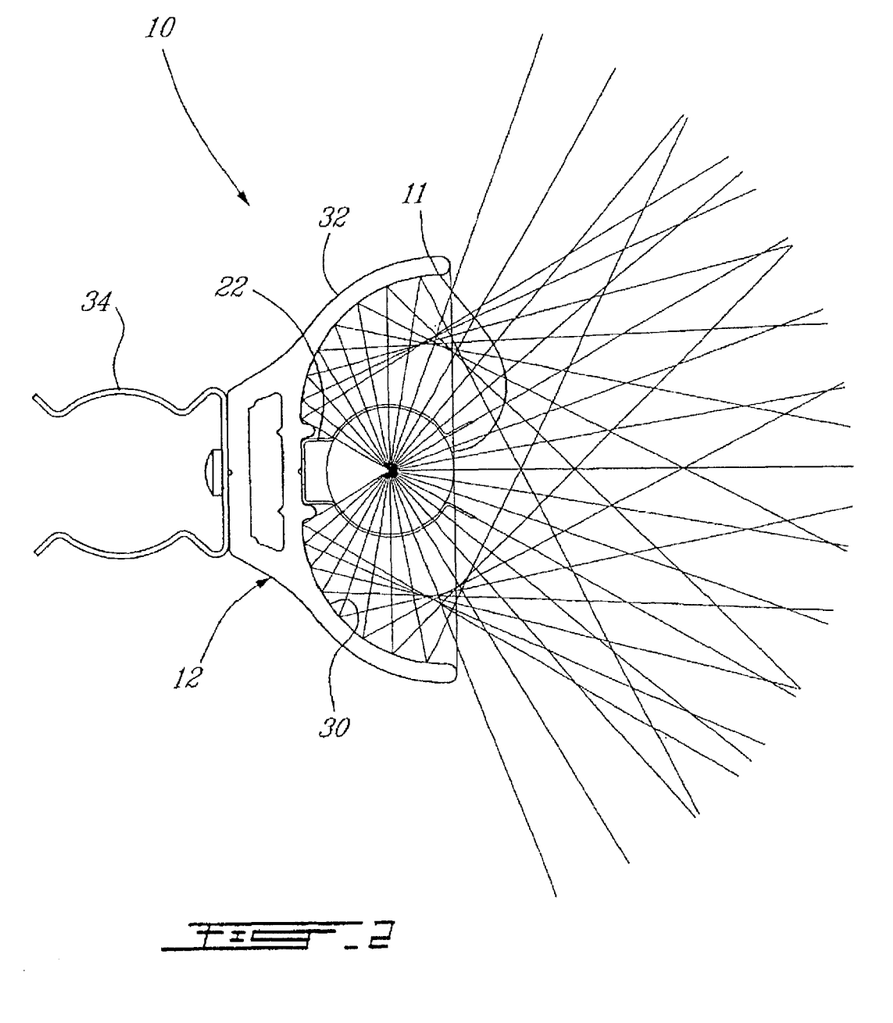
FIG. 2 is a sectional view taken along line 2-2 of FIG. 1.

A first embodiment of an assembly including a UV lamp and a reflector/shield assembly according to the present invention, illustrated in FIGS. 1 to 3, is designed to be used with a large commercial type HVAC coil that is mounted vertically within the air handler and in most instances is rectangular in shape.

With this type of coil, when condensation forms on the coil, it runs towards the ground. The bacteria and mold present in the air will settle and grow in the warm condensed water using various air born dust as nutrient.

Generally stated, the first embodiment of the present invention is concerned with an apparatus wherein a germicidal lamp is positioned within a generally parabolic reflector/shield assembly and the lamp and reflector/shield assembly are positioned in a particular manner relative to a HVAC condensing coil such that the coil is subjected to UVC radiation.

As will be further described hereinbelow, according to a further preferred embodiment of the present invention, the ultraviolet lamp is designed in the shape of an L. By using an L-shaped lamp, it is possible to treat the coil both horizontally and vertically at the same time with the same lamp.

Turning now to the appended FIGS. 1 to 3, an assembly 10 including a UV lamp 11 provided with a reflector/shield 12 will be described.

As can be better seen from FIG. 1, the lamp 11 is generally L-shaped, including a rounded portion 14. The lamp 11 includes a proximate end 16 provided with a conventional connector 18 and a distal end 20.

The lamp 11 is mounted to the reflector/shield 12 via internal clips 22. These clips 22 are better seen from FIG. 2. It is to be noted that clips having different base lengths could be used to change the relative position of the lamps with respect to the reflector/shield assembly to thereby modify the illumination pattern of the lamp.

The reflector/shield 12 is made of two identical portions 24 and 26 joined at right angle via a corner plate 28. As will readily be understood by one skilled in the art, the reflector/shield 12 is advantageously made of a material that adequately reflects UV radiation.

As can be better seen from FIG. 2 of the appended drawings, the reflector/shield 12 includes a generally parabolic inner surface 30 and a generally convex outer surface 32.

The inner surface 30 thereby so reflects the UV radiation emitted by the lamp 11 as is schematically illustrated in FIG. 2. The shape of the inner surface 30 and the position of the lamp 11 with respect to this inner surface are such that the illumination pattern is less that 180 degrees, thereby facilitating the orientation of the assembly to yield the desired illumination pattern.

The outer surface 32 is such that, when the lamp and reflector assembly of the present invention is positioned upstream from the coil in a HVAC system, the air flow will be deflected, thereby preventing cooling of the lamp 11.

FIG. 2 also illustrates an external clip 34 used to removably mount the reflector/shield 12 to a support as will be described hereinbelow with respect to FIG. 3.

FIG. 3 illustrates, in a perspective view, a system of four UV lamp assemblies 10a-10d that are so mounted to a support 36 that they are positioned upstream from and facing a coil 38.

As can be clearly seen from this figure, the air flow 40 from the HVAC system impinges on the outer convex surface of the reflector/shield and is therefore deflected therefrom, thereby shielding the UV lamps contained therein.

As will readily be understood by one skilled in the art, the four assemblies 10a-10d are so mounted to the support 36 that the illumination provided is more intense in the lower portion of the coil 38 and in the lower corners.

It is however to be noted that since the assemblies 10a-10d are mounted to the support 36 via clips 34 (see FIG. 2), it is easy to modify this illumination pattern to suit the needs of the user.

It is also to be noted that while the support 36 is illustrated as being a movable support, the circular cross-section tubes used to make this support could be permanently mounted to the internal surface (not shown) of the HVAC system.

Advantages

The fact that the lamp is in the shape of an L, the position of the lamp facing the coil can be adjusted for the size and layout of coil by translating and/or rotating the lamp.

Each lamp can be individually rotated or moved horizontally or vertically to optimize the irradiation of the coil.

It has been demonstrated that the UV intensity emitted by a discharge tube lamp type such as the one used in the present invention increases significantly with its operating temperature. It is therefore advantageous to design such system to operate under conditions that provides the highest environmental temperature. An advantage of the system of the present invention is that it utilizes the higher temperatures of the return air before it is cooled by the HVAC coil to increase the efficiency of the irradiation.

Furthermore, a generally parabolic aluminum reflector/shield assembly that is an integral part of the invention is installed immediately upstream of the lamp in such a way that the lamp sits inside this aluminum reflector. The lamp is therefore protected against the convection cooling effect of the air stream. This covering effect of the reflector provides a higher lamp operating temperature than a lamp without a reflector. A lamp operating at a higher temperature will produce substantially higher amounts of ultraviolet light which irradiates the coil quicker and allows for the use of less lamps than is necessary with other conventional systems.

As well, the design of the reflector is an integral part of the invention. By using a generally parabolic reflector, the ultraviolet rays can be more or less focused onto the coil and consequently the irradiation pattern can be modified. The reflector is adjustable so that the distance from the lamp to the reflector can be increased or decreased in order to increase or decrease the spread of the reflected ultraviolet rays onto the coil. It will be advantageous to increase the spread when the lamps are located close to the coil due to retrofit constraints, and vice-versa when the lamps are installed at greater distance from the coil.

The present invention also defines a method to attach the L-shape reflector and lamp so that the installation and removal of the units can be performed in a timely and proper manner.

By utilizing the present invention, it is possible to overcome the shortcomings and limitations that have been apparent in the conventional use of the germicidal lamps. By utilizing the proper reflector and tamp arrangement, it is possible to place the present invention more than three feet from the coil and still have the coil irradiated whereby no bacteria and mold will grow on the coil. In addition, the present invention utilizes a 19 mm ultraviolet lamp and that the ultraviolet output will be in excess of 450 microwatts per square centimeter at 1 meter.

By utilizing the present invention, it is not necessary to use a lamp specifically designed to work in harsh environments as the reflector will shield the lamp from temperature changes and allow for a less expensive and longer life lamp. When facing the flow, the lamps can collect some oily aerosols and dirt that will further inhibit their UV emission over time. In the current embodiment of the present invention, the lamps are protected from the air stream by an aerodynamically shaped generally parabolic reflector having a convex outer surface. This reflector is designed to effectively protect the lamp against convective cooling as well as dirt and oily aerosols that will overtime degrade the lamp performance.

It has been found that longer lamp life expectancy is achievable by using the reflector/shield assembly of the present invention.

Figure 4:
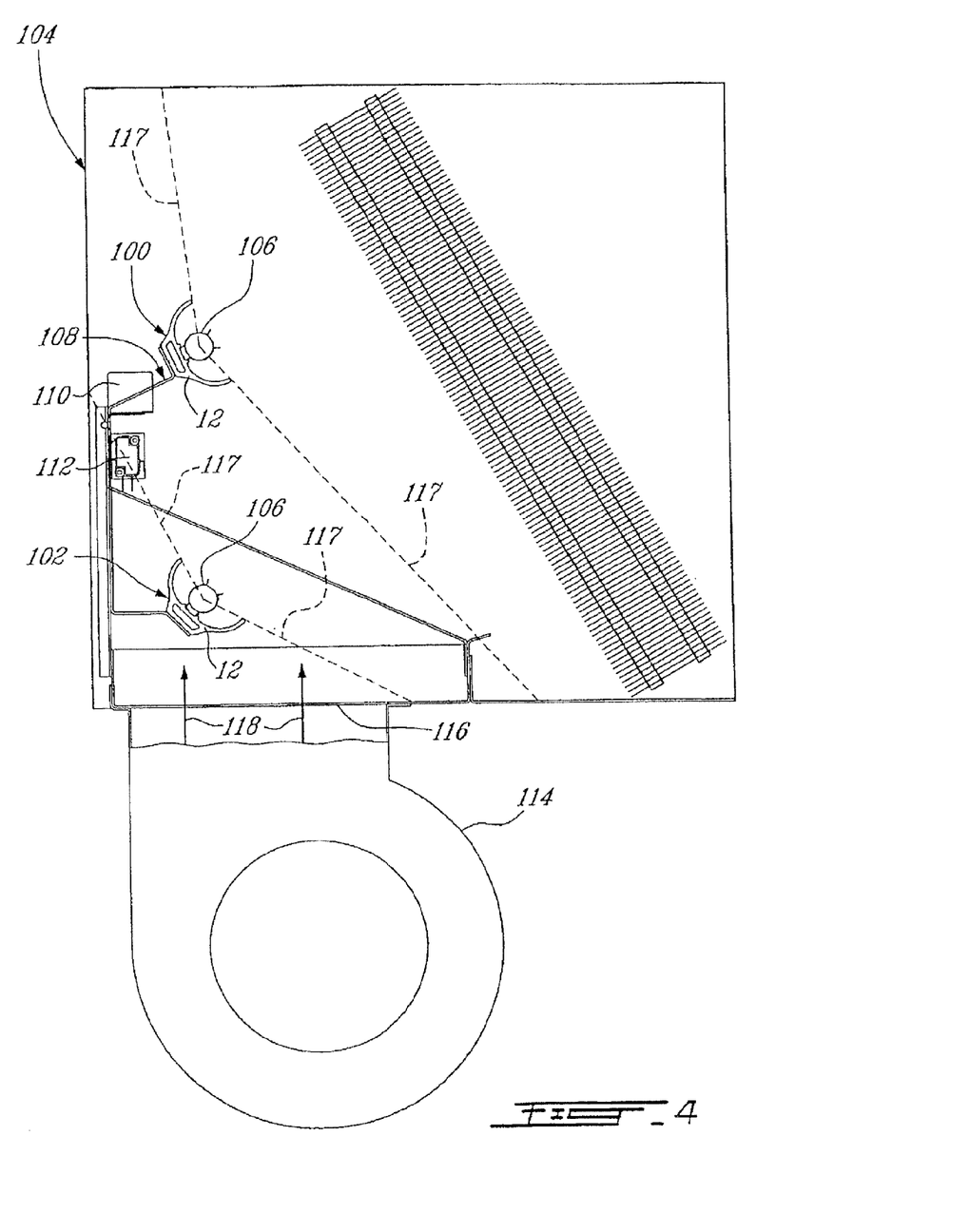
FIG. 4 is a sectional view of a second embodiment of the present invention where two UV lamps, each provided with a reflector/shield, are mounted in a window style air-conditioning unit.

Turning now to FIG. 4, a second use for straight UV lamp deflector/shield assemblies 100 and 102 according to a second embodiment of the present invention will be described. The assemblies 100 and 102 are shown mounted inside a conventional wall mountable air conditioning (A/C) unit 104 such as, for example, the Bard End-Mount Air Handler.

The assemblies 100 and 102 are very similar to the assembly 10 illustrated in FIGS. 1 to 3. The main difference between the assemblies 100, 102 and 10 is that the lamp 106 of the assemblies 100 and 102 is straight instead of being L-shaped.

The assemblies 100 and 102 are mounted to a bracket 108 that also mounts a ballast 110 and a safety switch 112 to the A/C unit 104. An electric motor 114 is so mounted to the A/C unit 104 as to blow air via an aperture 116.

An advantage of using the assemblies 100 and 102 in the A/C unit 104 is that the orientation of the assemblies may be so chosen that the motor 114 is not irradiated (see irradiation limits 117 in dashed lines). This is advantageous since it prevents the electrical windings of the motor 114 to be affected by continuous UV radiation exposure.

Again, one skilled in the art will notice that the assemblies 100 and 102 as so positioned that the outer convex surfaces of the reflector/shields 12 protect the lamps 106 from the airflow (see arrows 118).

Of course, even though two assemblies 100 and 102 are illustrated in FIG. 4, this number is given as a non-limiting example.

Turning now to FIGS. 5 to 8 of the appended drawings, an orientation/securing assembly 200 for a lamp assembly 201 (FIG. 6) comprising a straight UV lamp 202 a reflector/shield 204 and a ballast 206 will be described.

The orientation/securing assembly 200 is designed to be mounted to an existing A/C unit or to a duct for easy orientation and securing of an assembly 201 in an aperture done in the unit or duct.

Figure 5:
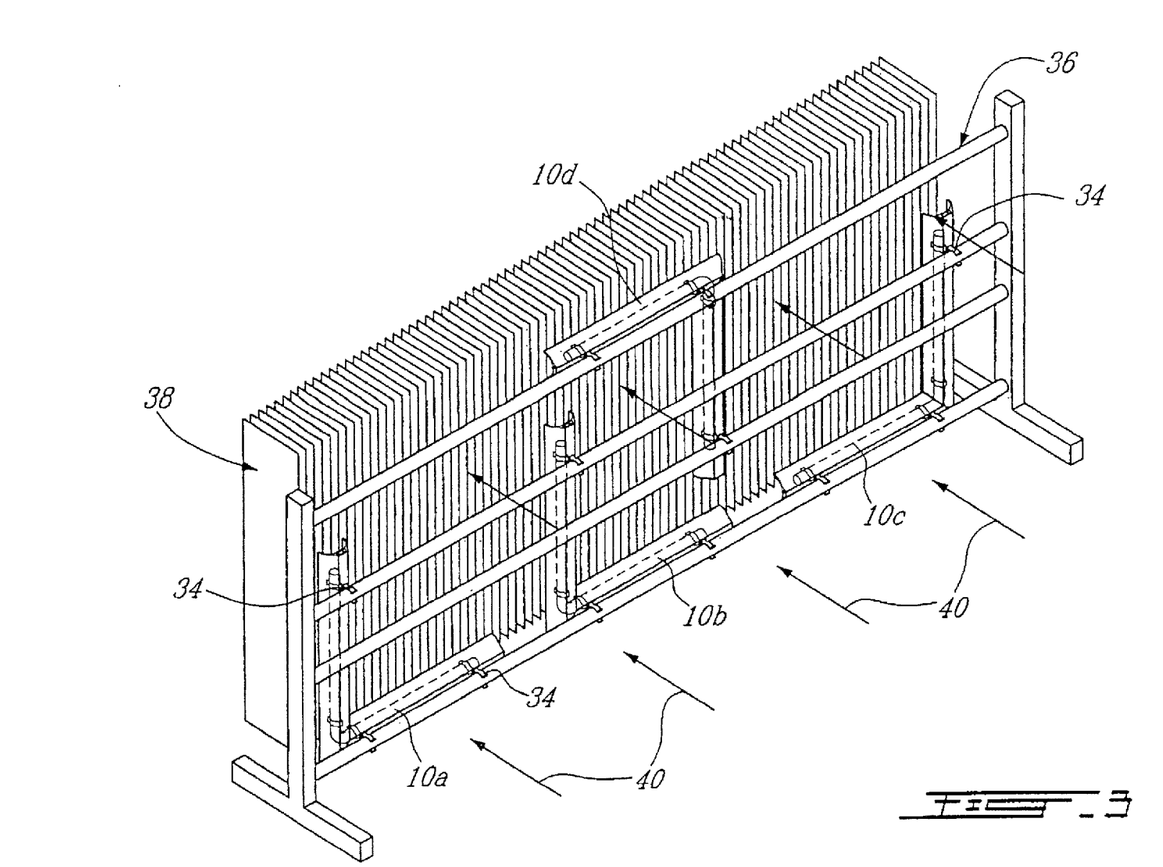
FIG. 5 is a front sectional view of a third embodiment of the present invention including one UV lamp provided with a reflector/shield and secured to an orienting and securing assembly.

The orientation/securing assembly 200 includes a weatherproof enclosure 208, a mounting plate 218, a supporting plate 210 and a lock 212.

Figure 6:
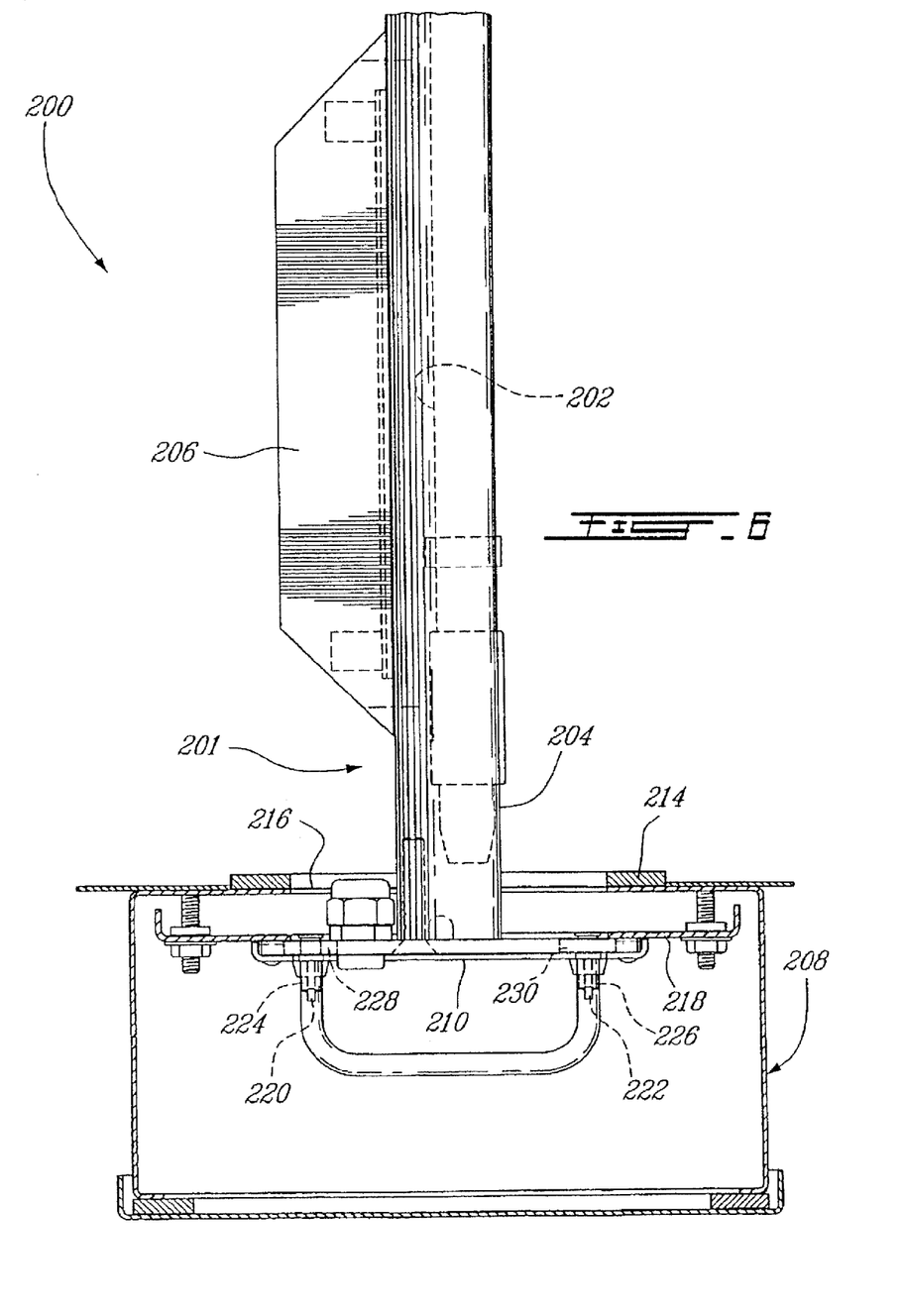
FIG. 6 is a sectional view taken along line 6-6 of FIG. 5.

As can be better seen from FIG. 6, the underside of the enclosure 208 is provided with weatherproofing material such as a foam gasket 214 enclosing the aperture 216 to thereby prevent the elements and unwanted debris to enter the enclosure 208 and the unit or duct to which the orientation/securing assembly 200 is mounted.

The mounting plate 218 is secured to the enclosure 208 to receive the other elements. The supporting plate 210 is so mounted to the mounting plate 218 via wing nuts 220, 222 secured to corresponding bolts 224, 226 fixed to the mounting plate 218, as to pivot between a non securing position illustrated in FIG. 7 and a securing position illustrated in FIG. 8. Thick washers 228, 230 are provided on the bolts 224, 226 between the plates 218 and 210. Finally, leaf springs 232, 234 (FIG. 5) are provided between the two plates 218 and 210 to bias the supporting plate 210 to its receiving position illustrated in FIG. 7.

Figure 7:
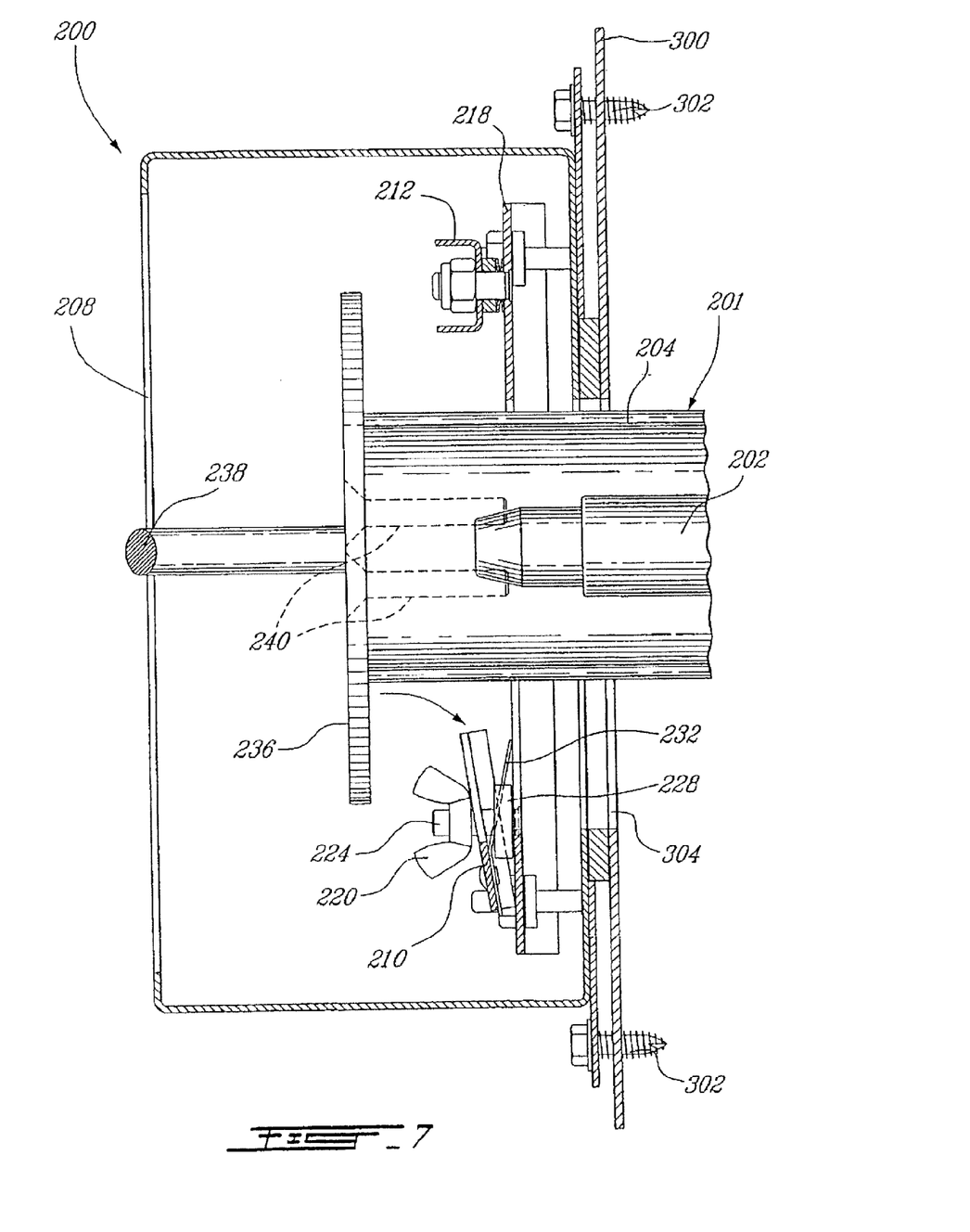
FIG. 7 is a side elevational view of the orienting and securing assembly of FIG. 5, shown before a UV lamp is inserted thereto.

Finally, as can be better seen from FIG. 7, a round reflector/shield support 236 provided with a handle 238 is secured to the reflector/shield 204 via fasteners 240.

The installation of a orientation/securing assembly 200 to an A/C unit will now be briefly described with reference to FIGS. 7 and 8.

FIG. 7 illustrates the enclosure 208 mounted to the wall 300 of an A/C unit or a duct via fasteners 302. An aperture 304 having been previously made in the wall 300 to allow the assembly 201 therethrough.

The assembly 201 is inserted in the aperture 304 as illustrated in FIG. 7. The support 236 is then so inserted behind the plate 210 as to rest onto the thick washers 228 that are used as bearings to allow rotation of the assembly 201 via the rotation of the handle 238.

Figure 8:
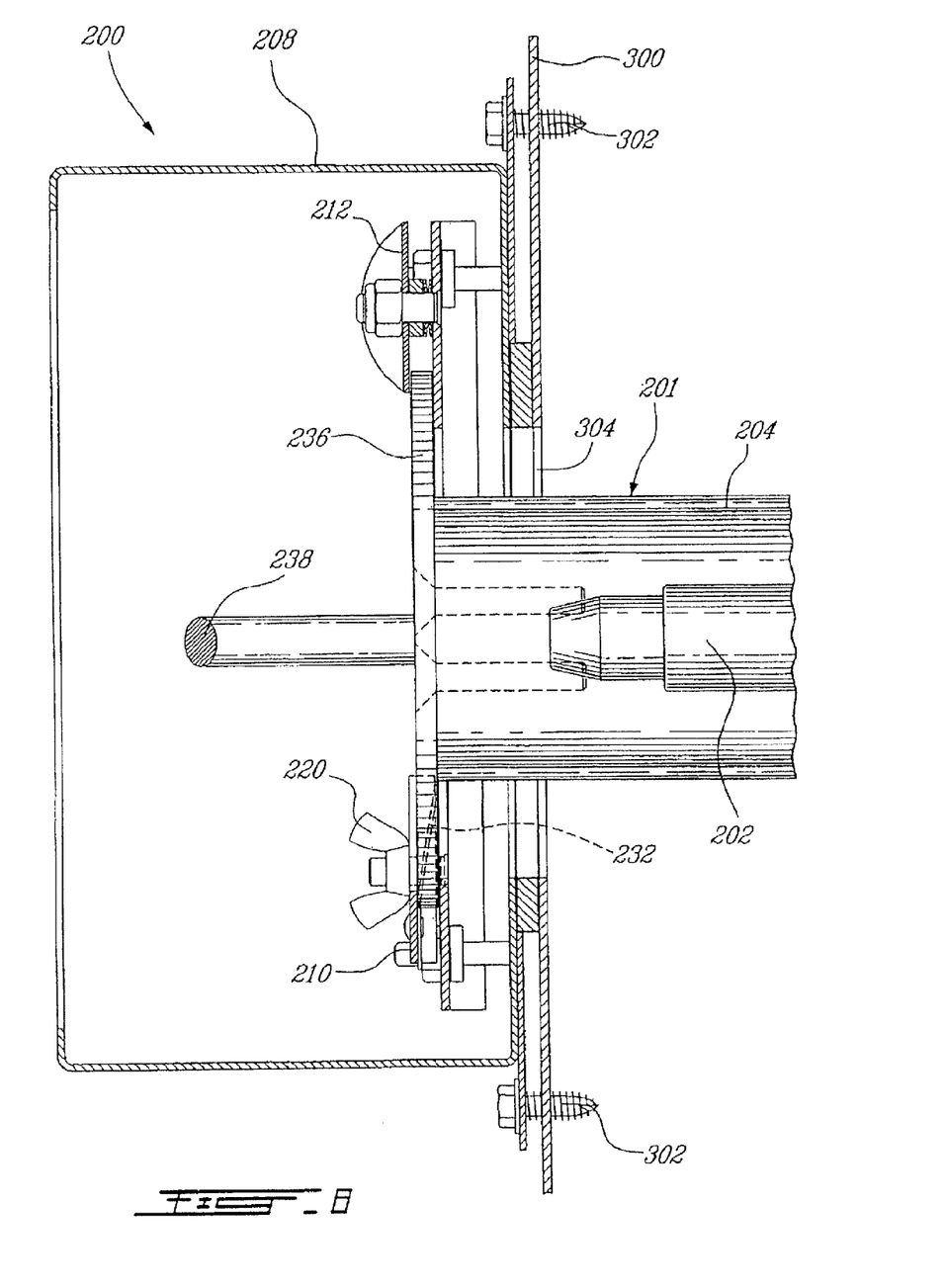
FIG. 8 is a side elevational view of the orienting and securing assembly of FIG. 5, shown after a UV lamp is inserted thereto.

The wing nuts 220 are then tightened and the lock 212 is rotated in its locking position to achieve the position illustrated in FIG. 8. It is to be noted that FIG. 8 is a sectional view taken along line 8-8 of FIG. 5.

As will easily be understood by one skilled in the art, the installation of the ballast 206 onto the reflector/shield 204 is advantageous since it places the ballast 206 in a well ventilated area, increasing therefore its useful life by preventing overheating.

It is to be noted that the use of a weatherproof enclosure is not required, should the orientation/securing assembly 200 be mounted inside a building or at another location that is not subject to the elements.

It is also to be noted that other types of UV lamp assemblies (not shown) could be used with the orienting and securing assembly of FIGS. 5 to 8. Indeed, this aspect of the present invention is not limited by the actual UV lamp and reflector/shield assembly shown herein.

Figure 9:
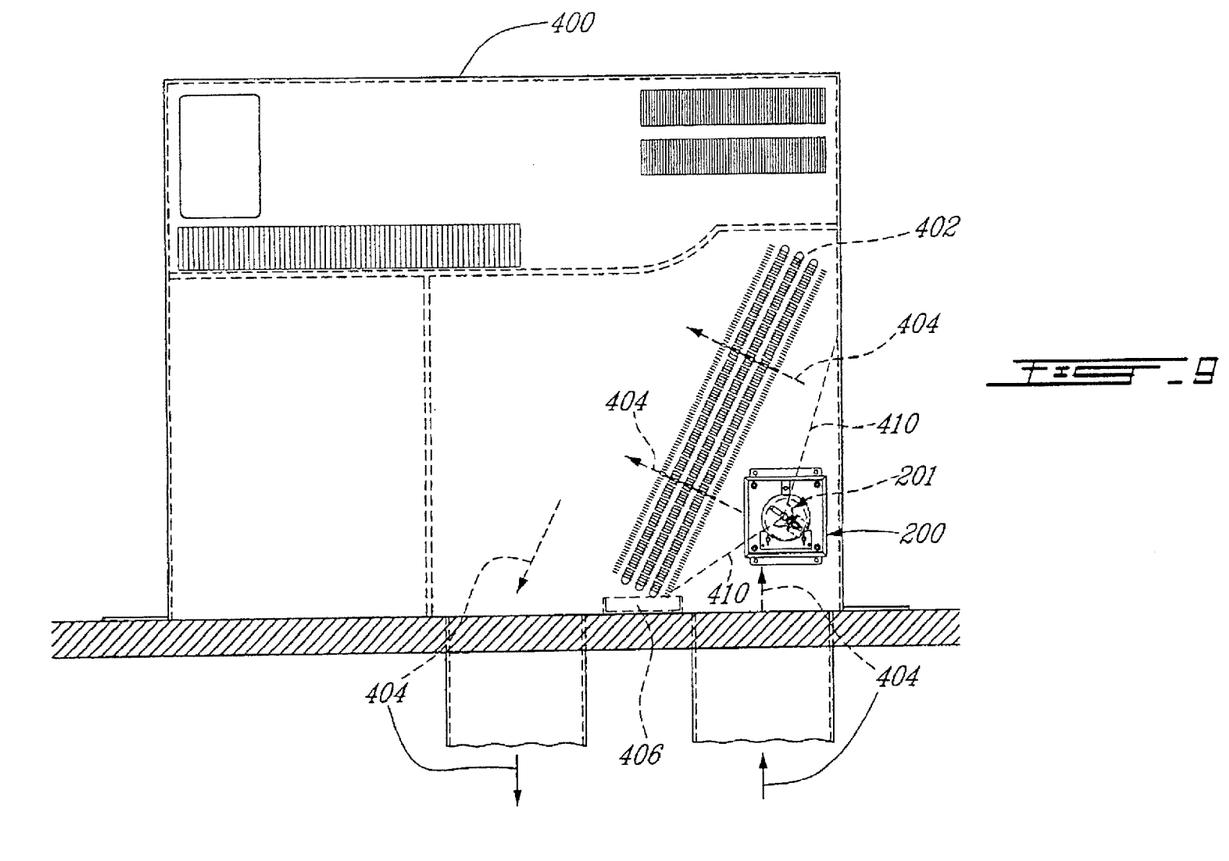
FIG. 9 is a schematic side elevational view of a rooftop air conditioning unit provided with one UV lamp mounted in an orienting and securing assembly, the lamp being positioned downstream from the coil.
Figure 10:
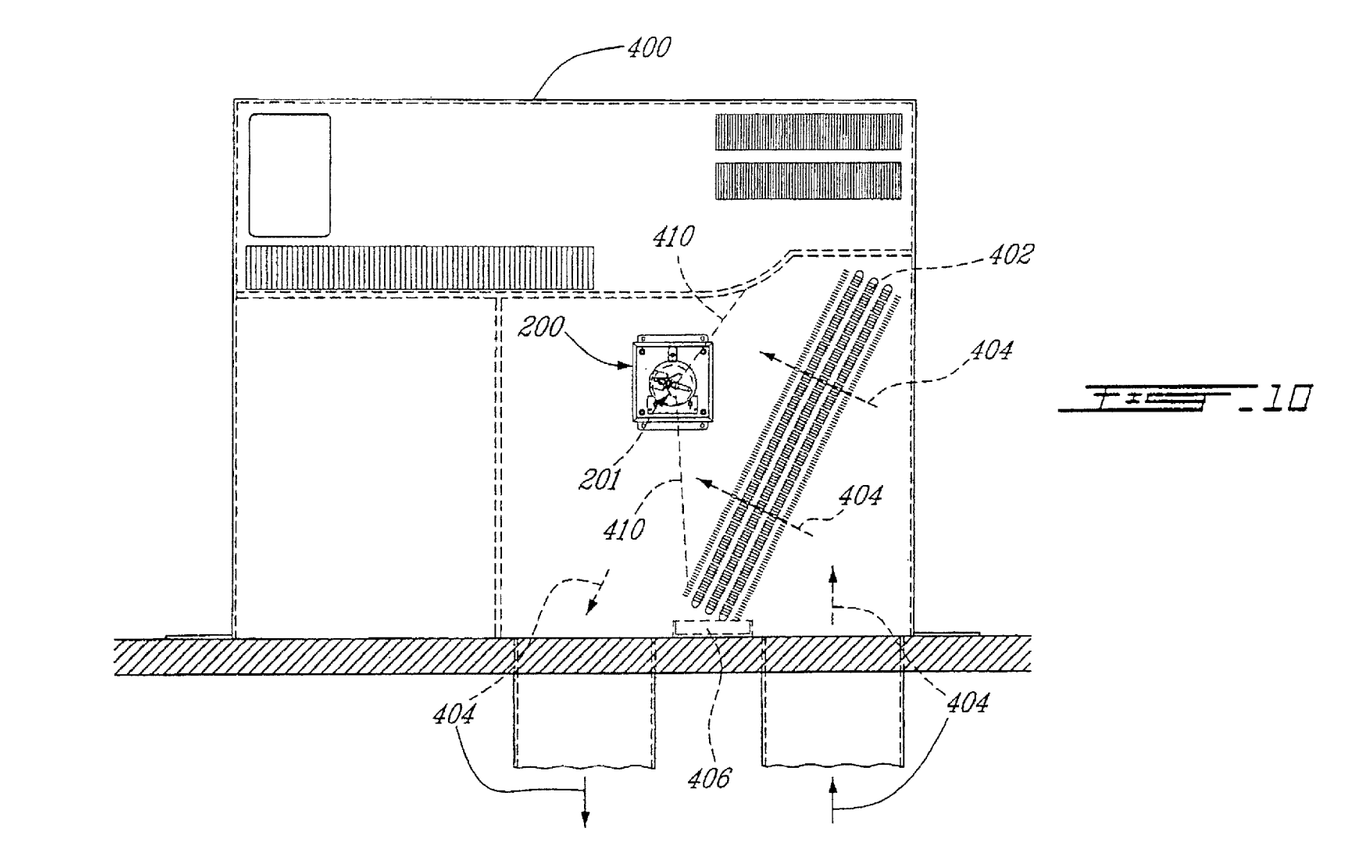
FIG. 10 is a schematic side elevational view of a rooftop air conditioning unit provided with one UV lamp mounted in an orienting and securing assembly, the lamp being positioned upstream from the coil.

Turning finally to FIGS. 9 and 10 of the appended drawings, two possible positions of the assembly 201 in a rooftop mounted A/C unit 400 will be described.

More specifically, FIG. 9 illustrates the orientation/securing assembly 200 and the lamp assembly 201 positioned downstream from the coil 402 (see flow arrows 404). It is to be noted that the assembly 201 is so positioned that the UV radiation does not reach the drain pan 406 (see irradiation limits 408 in dashed lines). This is an advantage since drain pans are often made of a material sensitive to UV radiation such as, for example, plastic.

On the other hand, FIG. 10 illustrates the orientation/securing assembly 200 and the lamp assembly 201 positioned upstream from the coil 402. It is to be noted that this position is not optimal since the reflector/shield operates as a reflector only, therefore reducing the useful life of the UV lamp. It is also to be noted that the assembly 201 is positioned so as not to irradiate the drain pan 406 (see irradiation limits 410 in dashed lines).

As will easily be understood by one skilled in the art, the reflector/shields 12 and 204 are advantageously made via an extrusion process of an extrudable material such as, for example aluminum.

Although the present invention has been described hereinabove by way of preferred embodiments thereof, it can be modified, without departing from the spirit and nature of the subject invention as defined in the appended claims.

What is claimed is:

1. An ultra-violet lamp assembly for an HVAC or A/C unit having a condenser coil with air flow moving from an upstream position relative to the condenser coil to a downstream position relative to the condenser coil, the assembly comprising:
   a support positioned upstream relative to the coil;
   an ultra violet lamp for emitting UV radiation on the condenser coil; and
   a reflector/shield extending along the length of the ultra-violet lamp and comprising:
   an inner reflector surface comprising a parabolic configuration, the ultraviolet lamp being adjustably mountable to the inner reflector surface so as to sit therein thereby providing a uniform illumination pattern on the condenser coil, the inner reflector surface providing reflecting UV radiation on the ultra-violet lamp thus preventing cooling thereof; and
   an outer shield surface comprising a convex configuration and being mountable to the support, the convex outer shield surface provides for air flow in the vicinity of the ultra-violet lamp to be deflected thereby thus preventing cooling of the ultra-violet lamp;
   wherein the distance between the UV lamp and the inner reflector shield can be adjusted to increase or decrease the spread of the reflected radiation on the condenser coil.

2. An ultra-violet lamp assembly according to claim 1, wherein the inner surface comprises aluminium.

3. An ultra-violet lamp assembly according to claim 1, wherein the support comprises an orienting and securing assembly.

4. An ultra-violet lamp assembly according to claim 1, further comprising a ballast mounted to the outer surface so as to be ventilated by the air flow.

5. An ultra violet lamp assembly for an HVAC or A/C unit comprising an air handler and a condenser coil therein, the assembly comprising:
   an ultra-violet lamp for being so positioned within the air handler relative to the condenser coil as to subject the condenser coil to ultra-violet radiation; and
   a reflector/shield for being mountable within the air handler and comprising:
   an inner reflector surface comprising a parabolic configuration, the ultraviolet lamp being adjustably mountable to the inner reflector surface, so as to sit therein thereby providing a uniform illumination pattern on the condenser coil, the inner reflector surface providing reflecting UV radiation on the ultra-violet lamp thus preventing cooling thereof; and
   an outer shield surface comprising a convex configuration and being, the convex outer shield surface provides for air flow in the vicinity of the ultra-violet lamp to be deflected thereby thus preventing cooling of the ultra-violet lamp,
   wherein the distance between the UV lamp and the inner reflector shield can be adjusted to increase or decrease the spread of the reflected radiation on the condenser coil.

6. A system comprising:
   an air handler;
   a condenser coil positioned within the air handler;
   an ultra-violet lamp assembly positioned within the air handler, the assembly comprising an ultra-violet lamp so positioned relative to the condenser coil as to subject the condenser coil to ultra-violet radiation; and a reflector/shield mounted within the air handler and comprising an inner reflector surface comprising a parabolic configuration, the ultraviolet lamp being adjustably mountable to the inner reflector surface, so as to sit therein thereby providing a uniform illumination pattern on the condenser coil, the inner reflector surface providing reflecting UV radiation on the ultra-violet lamp thus preventing cooling thereof; and an outer shield surface comprising a convex configuration, the convex outer shield surface provides for air flow in the vicinity of the ultra-violet lamp to be deflected thereby thus preventing cooling of the ultra-violet lamp; and
   at least one of an HVAC system and an A/C system,
   wherein the distance between the UV lamp and the inner reflector shield can be adjusted to increase or decrease the spread of the reflected radiation on the condenser coil.

* * * * *